United States Patent
Kim et al.

(10) Patent No.: US 12,403,304 B2
(45) Date of Patent: Sep. 2, 2025

(54) HIGH FREQUENCY AND ULTRASONIC FUSION TREATMENT DEVICE

(71) Applicant: WONTECH Co., Ltd., Daejeon (KR)

(72) Inventors: Jong Won Kim, Seongnam-si (KR);
Jung Hyun Kim, Seongnam-si (KR);
Young Seok Seo, Sejong-si (KR);
Young Sik Kim, Daejeon (KR)

(73) Assignee: WONTECH CO., LTD., Daejeon (KR)

( * ) Notice: Subject to any disclaimer, the term of this patent is extended or adjusted under 35 U.S.C. 154(b) by 465 days.

(21) Appl. No.: 18/059,382

(22) Filed: Nov. 28, 2022

(65) Prior Publication Data

US 2023/0338730 A1    Oct. 26, 2023

(30) Foreign Application Priority Data

Apr. 21, 2022    (KR) .......................... 10-2022-0049602

(51) Int. Cl.
*A61N 1/06*    (2006.01)
*A61N 1/32*    (2006.01)
*A61N 7/00*    (2006.01)

(52) U.S. Cl.
CPC ............... *A61N 1/06* (2013.01); *A61N 1/328* (2013.01); *A61N 7/00* (2013.01); *A61N 2007/0034* (2013.01)

(58) Field of Classification Search
CPC .. A61N 1/06; A61N 1/328; A61N 2007/0034; A61N 2007/0091; A61N 2007/025; A61N 7/00; A61N 7/02
See application file for complete search history.

(56) References Cited

U.S. PATENT DOCUMENTS

| | | | |
|---|---|---|---|
| 2009/0254008 A1* | 10/2009 | Shields, Jr. .............. | A61N 7/00 601/3 |
| 2016/0038771 A1* | 2/2016 | Jung ........................ | A61N 7/02 601/3 |
| 2017/0333705 A1* | 11/2017 | Schwarz ................. | A61N 1/328 |
| 2021/0393992 A1* | 12/2021 | Ji ............................ | A61N 1/403 |

\* cited by examiner

*Primary Examiner* — Tigist S Demie
(74) *Attorney, Agent, or Firm* — Harvest IP Law, LLP

(57) ABSTRACT

Proposed is a high frequency wave and ultrasonic wave fusion treatment device used for skin treatment and improvement that includes a housing, a tip disposed at one end of the housing, a plurality of high frequency wave transfer parts disposed on the tip and configured to transfer high frequency wave energy to skin in a pulsed manner, an ultrasonic wave transfer part disposed on the tip, but spaced apart from the high frequency wave transfer parts, and configured to transfer generated ultrasonic wave energy through an ultrasonic wave irradiation surface provided on the tip to the skin, and a movement part disposed inside the housing or the tip and configured to move the ultrasonic wave transfer part along the ultrasonic wave irradiation surface.

11 Claims, 8 Drawing Sheets

HIGH FREQUENCY AND ULTRASONIC FUSION TREATMENT DEVICE

CROSS REFERENCE TO RELATED APPLICATION

The present application claims priority to Korean Patent Application No. 10-2022-0049602, filed on Apr. 21, 2022, the entire contents of which is incorporated herein for all purposes by this reference.

BACKGROUND OF THE INVENTION

Field of the Invention

The present disclosure relates to a device and, more particularly, to a high frequency wave and ultrasonic wave fusion treatment device used for skin treatment and improvement.

Description of the Related Art

Recently, energy is provided to the skin using various energy sources, whereby a technique for treating the skin has been widely applied by transforming the tissue state of the skin or improving tissue characteristics. Skin treatment devices using various energy sources such as laser beams, flash lamps, ultrasonic waves, and the like have been developed, and recently, research on skin treatment devices using RF high frequency wave energy has been actively conducted. When high frequency wave energy is provided to the skin surface, each time a direction of a high frequency wave current is changed, molecules constituting skin tissue vibrate and rub against each other, and deep heat is generated by rotational motion, twisting motion, or collision motion. Such deep heat may increase the temperature of skin tissue to reorganize a collagen layer, thereby improving wrinkles and enhancing skin elasticity.

In addition, when ultrasonic wave energy is provided to the skin surface, high intensity ultrasonic wave energy is focused in one place, whereby high heat is generated. Using the heat generated by focused ultrasonic waves, specific subcutaneous tissue such as tumors in the skin and the like may be burned and removed, or degeneration and regeneration of the skin tissue may be caused, thereby improving wrinkles.

The foregoing is intended merely to aid in the understanding of the background of the present disclosure and is not intended to mean that the present disclosure falls within the purview of the related art that is already known to those skilled in the art.

SUMMARY OF THE INVENTION

Accordingly, the present disclosure has been made keeping in mind the above problems occurring in the related art, and an objective of the present disclosure is to provide a high frequency wave and ultrasonic wave fusion treatment device in order to treat and improve the skin by transferring high frequency wave energy and ultrasonic wave energy to the skin without continuous handpiece movement.

The objective of the present disclosure is not limited to the above-mentioned objective, and other objectives not mentioned may be clearly understood by those skilled in the art from the description below.

In order to achieve the above objective, according to one embodiment of the present disclosure, there may be provided a high frequency wave and ultrasonic wave fusion treatment device, the device including: a housing; a tip disposed at one end of the housing; a plurality of high frequency wave transfer parts disposed on the tip and configured to transfer high frequency wave energy to skin in a pulsed manner; an ultrasonic wave transfer part disposed on the tip, but spaced apart from the high frequency wave transfer parts, and configured to transfer generated ultrasonic wave energy through an ultrasonic wave irradiation surface provided on the tip to the skin; and a movement part disposed inside the housing or the tip and configured to move the ultrasonic wave transfer part along the ultrasonic wave irradiation surface.

In the one embodiment of the present disclosure, the plurality of high frequency wave transfer parts may be arranged symmetrically on opposite sides with the ultrasonic wave irradiation surface as a center.

In the one embodiment of the present disclosure, the high frequency wave transfer parts may be provided with one cover layer disposed on a surface of one side thereof facing the skin.

In the one embodiment of the present disclosure, the device may further include a controller configured to control at least one of the high frequency wave transfer parts, the ultrasonic wave transfer part, and the movement part.

In the one embodiment of the present disclosure, the controller may be configured to control the high frequency wave transfer parts and the ultrasonic wave transfer part so that the high frequency wave energy and the ultrasonic wave energy are emitted at the same time or at different times, respectively.

In the one embodiment of the present disclosure, the controller may be configured to control an emission sequence and an emission time point of the high frequency wave energy of each of the high frequency wave transfer parts on the basis of an arrangement order of the plurality of high frequency wave transfer parts.

In the one embodiment of the present disclosure, the controller may be configured to control at least one pair of the high frequency wave transfer parts disposed symmetrically with each other with respect to the ultrasonic wave irradiation surface among the plurality of high frequency wave transfer parts to simultaneously emit high frequency wave energy.

In the one embodiment of the present disclosure, the controller may be configured to group the plurality of high frequency wave transfer parts into a plurality of groups and control emission of the high frequency wave energy for each group.

In the one embodiment of the present disclosure, the controller may be configured to control an emission sequence and an emission time point of the high frequency wave energy on the basis of an arrangement order of the plurality of groups.

In the one embodiment of the present disclosure, the controller may be configured to control a movement distance and a movement time of the movement part on the basis of the emission sequence and emission time point of the high frequency wave energy.

In the one embodiment of the present disclosure, the controller may be configured to control movement of the movement part so that the ultrasonic wave transfer part emits ultrasonic wave energy at a position staggered with the high frequency wave transfer part emitting high frequency wave energy among the plurality of high frequency wave transfer parts.

As described above, according to an embodiment of the present disclosure, a thermal effect can be maximized by irradiating skin with high frequency wave energy and ultrasonic wave energy simultaneously or alternately.

In addition, even when the skin is irradiated with high frequency wave energy and ultrasonic wave energy simultaneously, damage to the skin can be avoided.

Effects of the present disclosure are not limited to the above effects and should be understood to include all effects that can be inferred from the description of the present disclosure or the configuration of the invention described in the claims.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
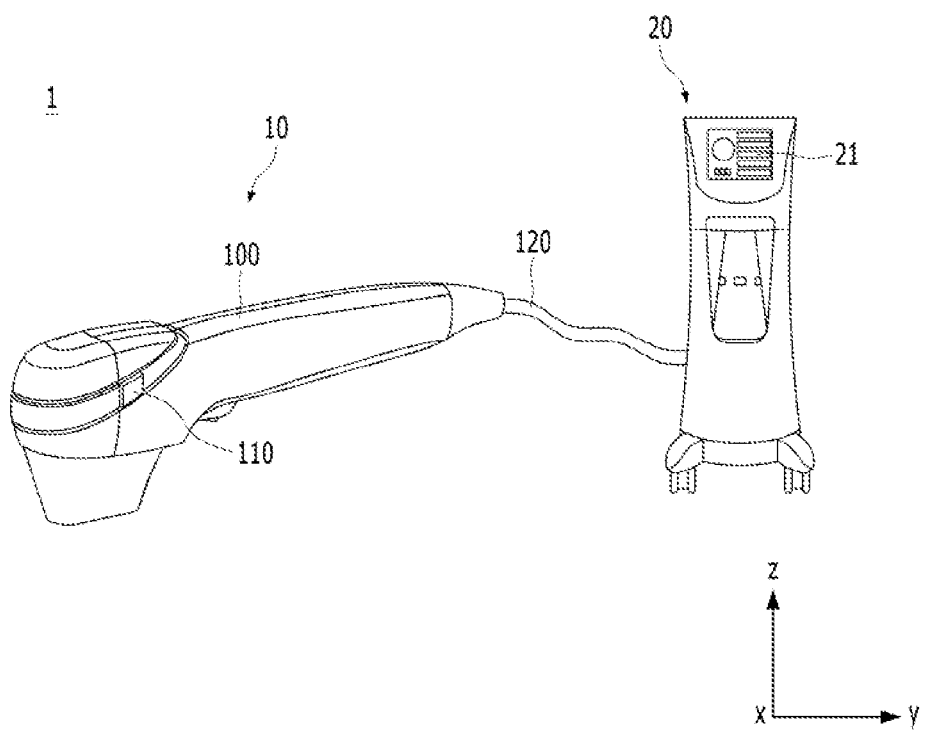
FIG. 1 is a view showing a high frequency wave and ultrasonic wave fusion treatment device according to an embodiment of the present disclosure.

Hereinbelow, the present disclosure will be described with reference to the accompanying drawings. However, the present disclosure may be embodied in many different forms and, therefore, is not limited to embodiments described herein. In addition, in order to clearly explain the present disclosure in the drawings, parts irrelevant to the description are omitted, and similar reference numerals are attached to similar parts throughout the specification.

Throughout the specification, when a part is said to be "connected (accessed, contacted, coupled)" with another part, this includes not only "directly connected", but also "indirectly connected" with another member in between. In addition, when a part "includes" a certain component, it means that it may further include other components without excluding other components unless otherwise stated.

Terms used in the present specification are only used to describe specific embodiments and are not intended to limit the present disclosure. Singular expressions include plural expressions unless the context clearly dictates otherwise.

In the present specification, terms such as "include", "have", and the like are intended to designate that features, numbers, steps, operations, components, parts, or combinations thereof described in the specification exist and are to be understood such that presence or addition of one or more other features, numbers, steps, operations, components, parts, or combinations thereof is not precluded.

Hereinafter, the embodiments of the present disclosure will be described in detail with reference to the accompanying drawings.

Figure 2:
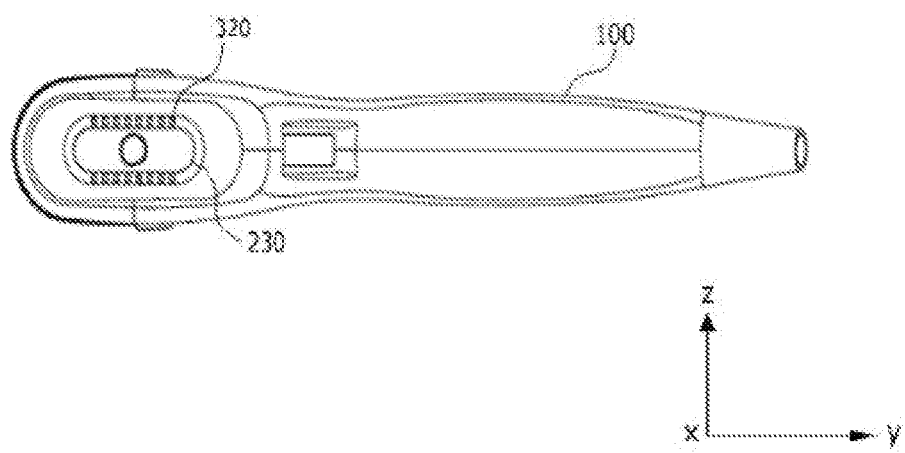
FIG. 2 is a view showing a tip end portion to which a Flexible Printed Circuit Board (FPCB) is attached according to the embodiment of the present disclosure.
Figure 3:
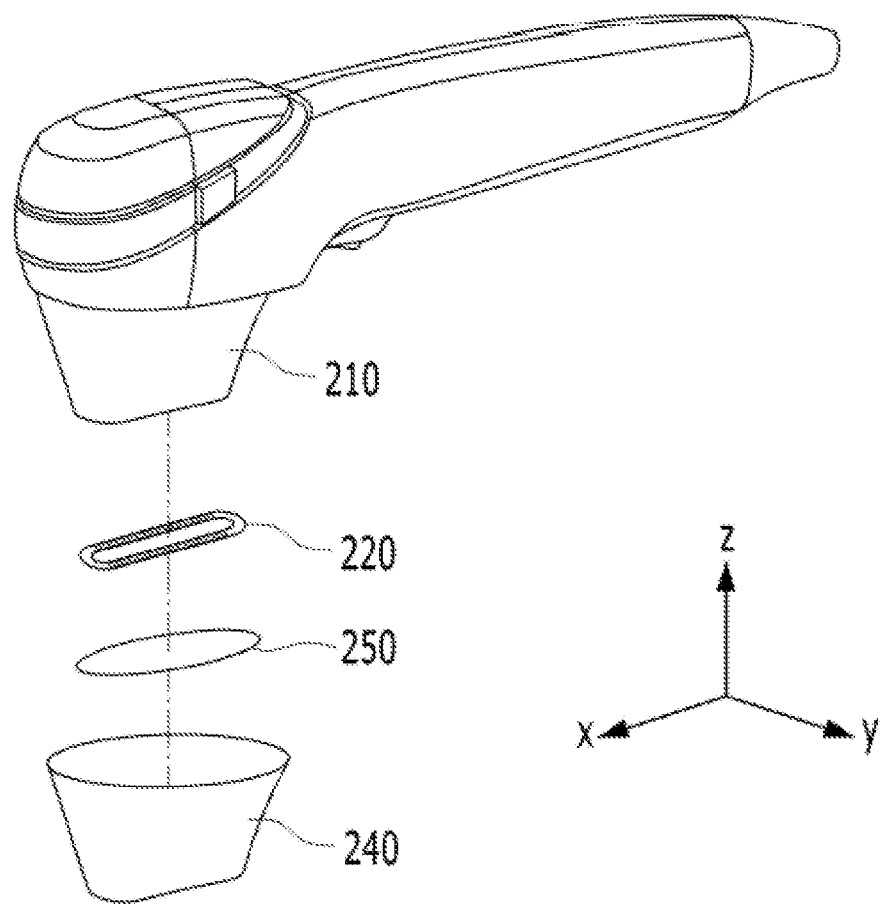
FIG. 3 is a view showing a handpiece having a cover and a cover layer according to the embodiment of the present disclosure.
Figure 4:
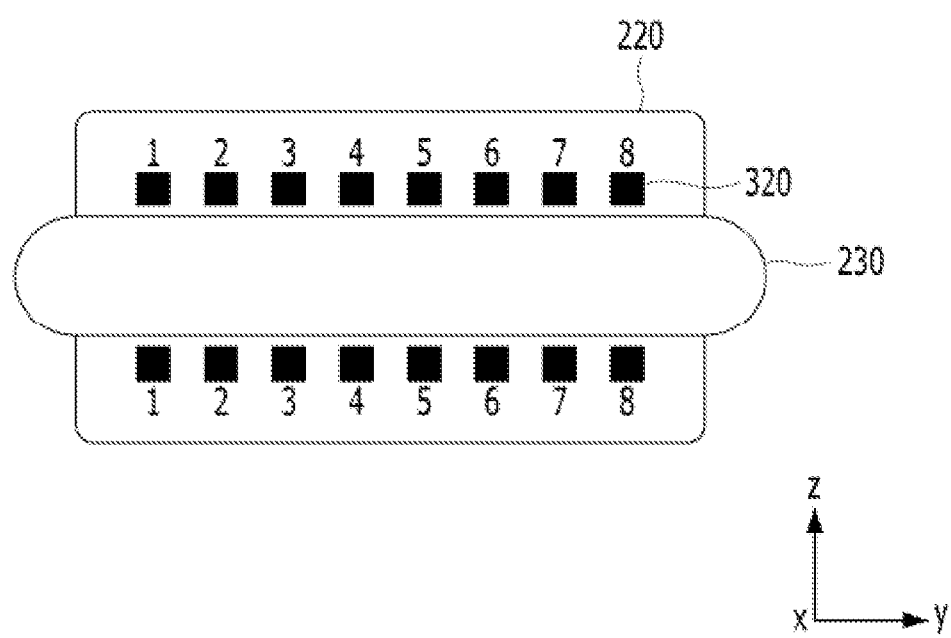
FIG. 4 is a sectional view showing a tip provided in a handpiece according to the embodiment of the present disclosure.
Figure 5:
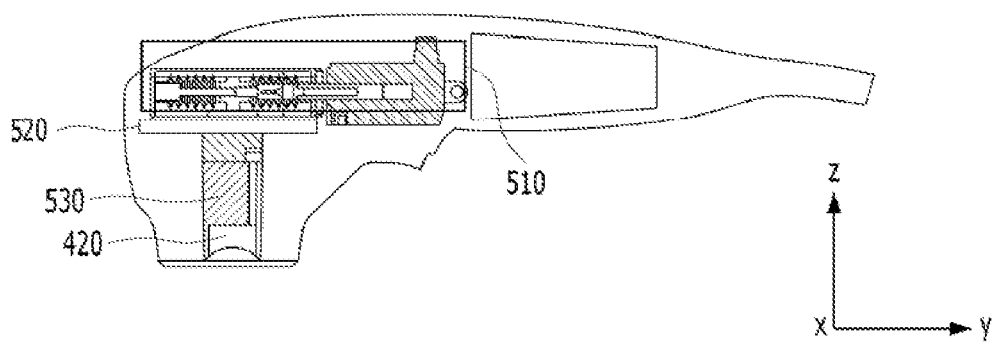
FIG. 5 is a block diagram schematically showing a control signal of a controller according to the embodiment of the present disclosure.
Figure 6:
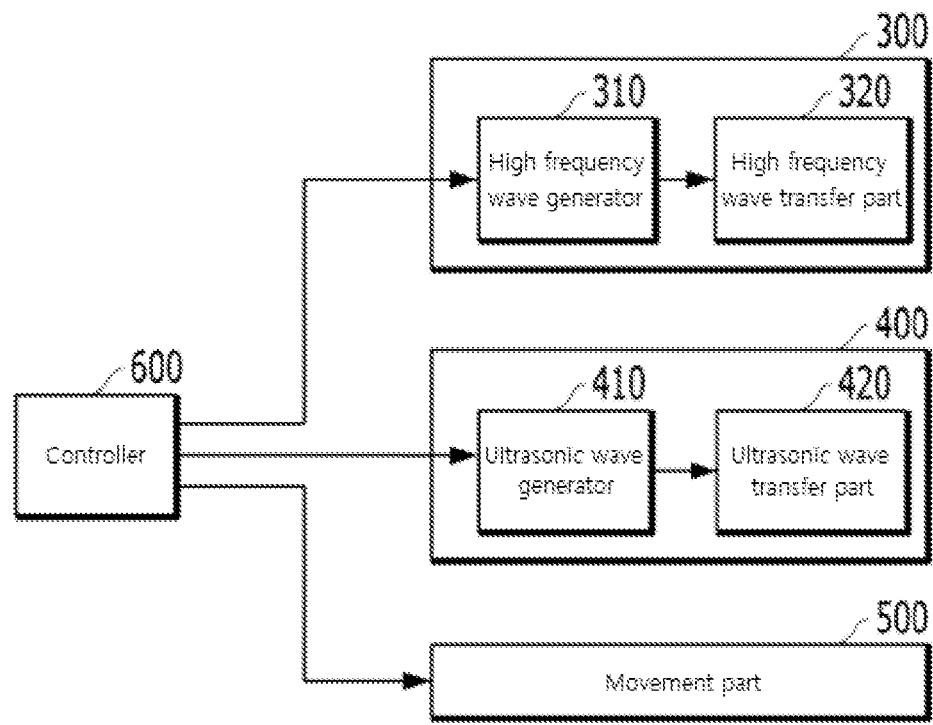
FIG. 6 is a view showing a movement part according to the embodiment of the present disclosure.
Figure 7:
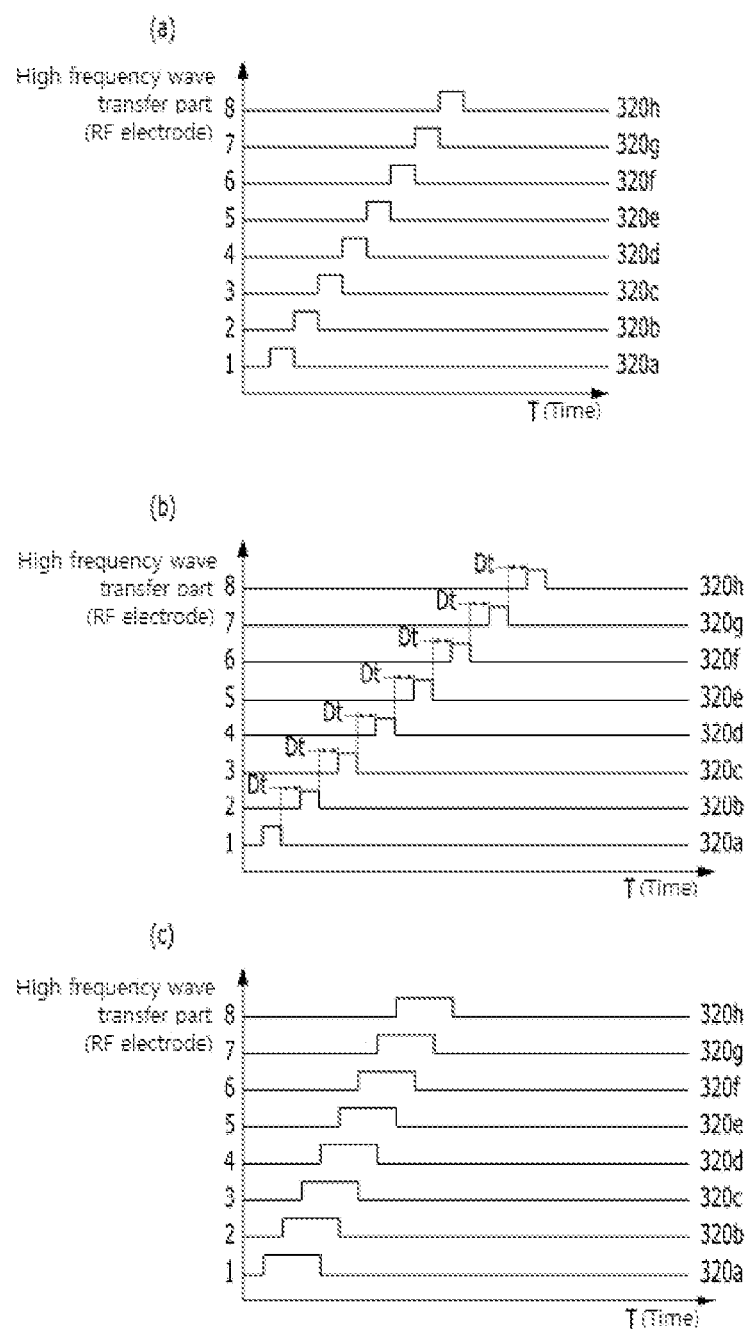
FIG. 7 shows operation patterns of the high frequency wave and ultrasonic wave fusion treatment device according to the embodiments of the present disclosure.
Figure 8:
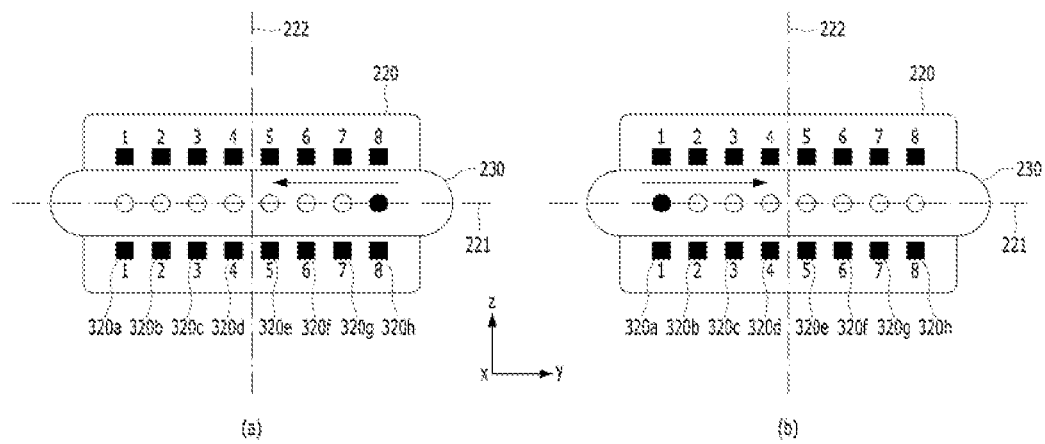
FIG. 8 is sectional views showing a tip provided in a handpiece according to another embodiment of the present disclosure.
Figure 9:
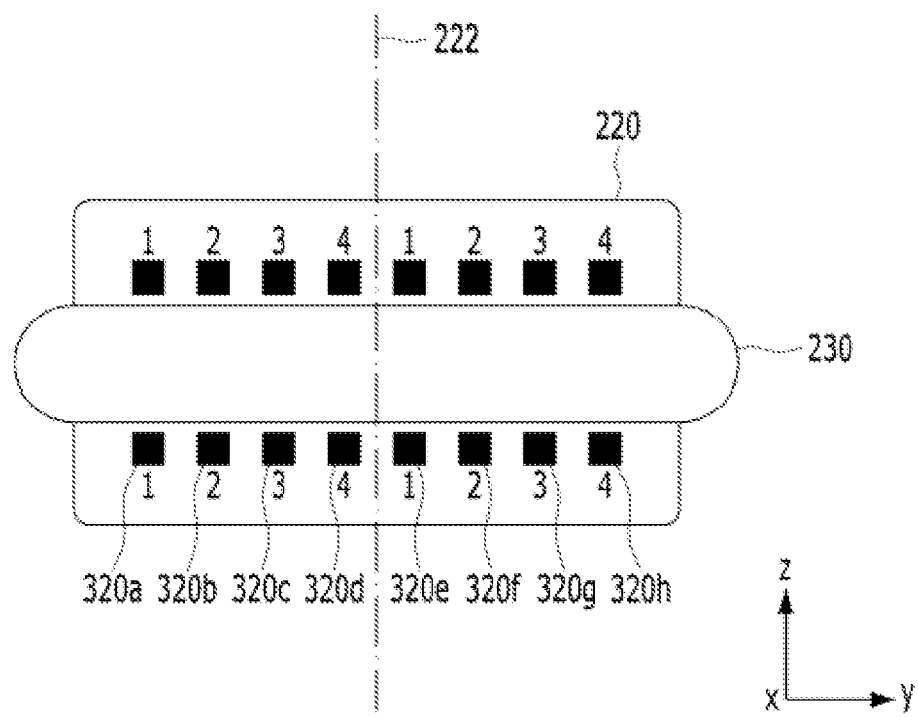
FIG. 9 is a sectional view showing a tip provided in the handpiece according to another embodiment of the present disclosure.
Figure 10:
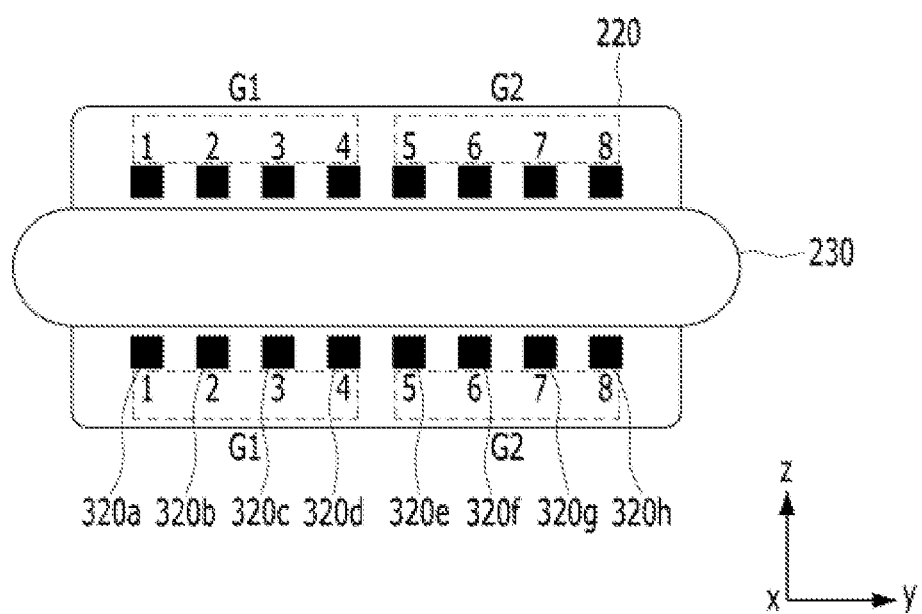
FIG. 10 is a sectional view showing a tip provided in the handpiece according to still another embodiment of the present disclosure.

FIG. 1 is a view showing a high frequency wave and ultrasonic wave fusion treatment device 1 according to an embodiment of the present disclosure, FIG. 2 is a view showing a tip end portion 220 to which a Flexible Printed Circuit Board (FPCB) is attached according to the embodiment of the present disclosure, FIG. 3 is a view showing a handpiece 10 having a cover 240 and a cover layer 250 according to the embodiment of the present disclosure, FIG. 4 is a sectional view showing a tip 200 provided in the handpiece 10 according to the embodiment of the present disclosure, FIG. 5 is a block diagram schematically showing a control signal of a controller 600 according to the embodiment of the present disclosure, FIG. 6 is a view showing a movement part 500 according to the embodiment of the present disclosure, a part (a) of FIG. 7 shows a first operation pattern of the high frequency wave and ultrasonic wave fusion treatment device 1 according to the embodiment of the present disclosure, a part (b) of FIG. 7 shows a second operation pattern of the high frequency wave and ultrasonic wave fusion treatment device 1, and a part (c) of FIG. 7 shows a third operation pattern of the high frequency wave and ultrasonic wave fusion treatment device 1, FIG. 8 is sectional views showing a tip 200 provided in a handpiece 10 according to another embodiment of the present disclosure, FIG. 9 is a sectional view showing a tip 200 provided in the handpiece 10 according to another embodiment of the present disclosure, and FIG. 10 is a sectional view showing a tip 200 provided in the handpiece 10 according to still another embodiment of the present disclosure.

With reference to FIGS. 1 to 10, the high frequency wave and ultrasonic wave fusion treatment device 1 may be a system in order to treat (improve) patient's skin using high frequency wave energy and/or ultrasonic wave energy. The high frequency wave and ultrasonic wave fusion treatment device 1 may include a handpiece and a main body 20.

The main body 20 is connected to the handpiece 10 and may generate high frequency wave energy and ultrasonic wave energy according to input information input by a user and transfer same to the handpiece 10. The main body 20 may include a display part 21, a high frequency wave generator 310, and an ultrasonic wave generator 410.

The display part 21 may display an image to the outside. The image displayed by the display part 21 may represent input information such as intensity of high frequency wave and ultrasonic wave energy, adjustment of pulse interval, or the like. The display part 21 may be disposed on an upper portion of the main body 20 so that the screen and the user face each other so as to be easily touched by the user. The display part 21 may decide input information about the high frequency wave energy and ultrasonic wave energy transferred to the handpiece 10 by a user touching a screen and an image.

The display unit 21 may be located on an outer surface of the main body 20. The display part 21 may be disposed on an upper portion of the main body 20 so that the screen and the user face each other so as to be easily touched by the user.

The high frequency wave generator 310 and the ultrasonic wave generator 410 will be described together with the handpiece 10 below.

The handpiece 10 may transfer high frequency wave energy and/or ultrasonic wave energy to patient's skin. The handpiece 10 may include a housing 100, a tip 200, a high frequency wave transfer part 320, an ultrasonic wave transfer part 420, and the movement part 500. In addition, the handpiece 10 may further include the controller 600.

The housing 100 is a part that a user grips when skin treatment is performed using the handpiece 10 and may be provided in a handheld type to improve convenience of user manipulation. For example, such a housing may have a rear end, which is an end of a side opposite to a front end, having a width wider than the front end at which the tip is disposed. At this time, a boundary portion between the front end and the rear end of the housing 100 is provided in a curved surface that is an incurvated shape, so the user may comfortably and stably hold the housing 100. The housing 100 may include a detachable portion 110 and a cable 120.

The detachable portion 110 may detach the tip 200 from the housing 100. More specifically, the detachable portion 110 may be selectively coupled to the tip 200. As one embodiment, one end of the detachable portion 110 may protrude to the outside of the housing 100 and an opposite end (not shown) may be accommodated inside the housing 100. At this time, the opposite end of the detachable portion 110 may be detachably coupled to the rear end (not shown) of the tip 200 (for example, the end portion opposite to the tip end portion 220 to be described later). In this case, when the user presses the detachable portion 110, the opposite end of the detachable portion 110 is separated from the rear end of the tip 200, whereby the tip 200 may be separated from the housing 100.

The cable 120 may be connected to the main body 20 and transfer power generated from the main body 20 to the handpiece 10. In addition, the cable 120 may transfer a high frequency wave signal and an ultrasonic wave signal to the handpiece 10.

The tip 200 may transmit both high frequency wave energy and ultrasonic wave energy to the patient's skin. In addition, the tip 200 may transmit the high frequency wave energy or the ultrasonic wave energy, respectively. Tip 200 may be disposed in the housing 100. In the one embodiment, the tip 200 may be disposed to face a bottom surface at the front end portion of the housing 100.

The tip 200 may be detachably coupled to the housing 100. As described above, the tip 200 is detachably coupled to the detachable portion 110 and may be separated from the housing 100 by, for example, an operation pressing the detachable portion 110. At this time, the tip 200 may include a tip body 210, the tip end portion 220, and an ultrasonic wave irradiation surface 230.

When coupled with the detachable portion 110, the tip body 210 may be a part that directly contacts one end of the detachable portion 110. The tip body 210 has a flat and angular cross section so as to be easily gripped by the user, thereby being allowed to be easily attached to and detached from the handpiece 10.

The tip end portion 220 may transfer ultrasonic wave energy and/or high frequency wave energy to the patient's skin during skin treatment using the handpiece 10. With reference to FIG. 2, the FPCB may be attached to the tip end portion 220. The FPCB is a non-conductive board, is a film of a synthetic resin material having flexibility, and may have various sizes and shapes depending on an area to be treated. However, the FPCB may have a shape that matches a shape of the tip end portion 220 as shown in FIG. 4. In one embodiment, with reference to FIG. 3, the FPCB may be provided with a cover 240 so as to be prevented from being separated from the tip end portion 220. The tip end portion 220 may be disposed to face the patient's skin during skin treatment.

The high frequency wave signal and the ultrasonic wave signal transferred through the cable 120 may be converted into high frequency wave energy and ultrasonic wave energy, thereby being subjected to irradiation through the tip end portion 220. At this time, the handpiece 10 may transfer the high frequency wave energy and/or ultrasonic wave energy with the tip end portion 220 in a state of being brought into contact with the skin. Meanwhile, as another embodiment, the tip end portion 220 may transfer the high frequency wave energy and ultrasonic wave energy in a non-contact state with the skin, but hereinafter, an embodiment in which the tip end portion 220 is brought into contact with the skin will be mainly described.

When the tip end portion 220 is brought into contact with the skin to be treated, the high frequency wave and ultrasonic waves may be simultaneously or alternately transferred to the skin being brought into contact with the tip. Details on this will be described later. The ultrasonic wave irradiation surface 230 may be a portion that the outside is irradiated with ultrasonic wave energy, having been generated from the ultrasonic wave transfer part 420, passing therethrough. When water is contained inside the tip 200, the ultrasonic wave irradiation surface 230 may prevent water from being discharged to the outside. In this case, the water is an ultrasonic wave energy transfer medium and may allow the ultrasonic wave energy to be smoothly generated and emitted in the ultrasonic wave transfer part 420. Such an ultrasonic wave irradiation surface 230 is disposed on the tip end portion 220 and may have a length the same as a length of a guide shaft 520 to be described later or a maximum moving distance of the ultrasonic wave transfer part 420.

As an embodiment, the ultrasonic wave irradiation surface 230 may extend from one side of the tip end portion 220 up to an opposite side facing thereto. At this time, when viewed from a direction parallel to the YZ plane, the ultrasonic wave irradiation surface 230 may pass through the center of the tip end portion 220 and extend in a direction parallel to a width direction (Y axis direction). The ultrasonic wave irradiation surface 230 may have a length the same as a moving distance of the ultrasonic wave transfer part 420. In this case, the ultrasonic wave transfer part 420 may transfer ultrasonic wave energy to the skin through a portion of the ultrasonic wave irradiation surface 230 while moving along the ultrasonic wave irradiation surface 230, which will be described in detail later.

A high frequency wave module 300 may generate high frequency wave energy and provide it to the skin. The high frequency wave module 300 may include the high frequency wave generator 310 and the high frequency wave transfer part 320.

The high frequency wave generator 310 may receive a control signal from the controller 600 to be described later and generate various types of high frequency wave energy on the basis of a received control signal. For example, the high frequency wave generator 310 may generate various types of high frequency wave energy having various specific time points, frequencies, and intensities. The high frequency wave generator 310 may transfer generated high frequency wave energy to the high frequency wave transfer part 320 inside the housing 100 through the cable 120.

The high frequency wave generator 310 may be disposed inside the main body 20. In such a case, the high frequency wave generator 310 may provide the generated high frequency wave energy to the handpiece 10 through the cable 120. Meanwhile, the present disclosure is not limited thereto, and as another embodiment, the high frequency wave generator 310 may also be disposed inside the housing 100.

The high frequency wave transfer part 320 may be connected to the high frequency wave generator 310 and transfer the high frequency wave energy generated by the high frequency wave generator 310 to the skin. The high frequency wave transfer part 320 may be, for example, a radio frequency (RF) electrode. In this case, when a plurality of high frequency wave transfer parts 320 is provided, high frequency wave energy having various frequencies and intensities may be transferred.

The high frequency wave transfer part 320 may be disposed on the tip 200. More specifically, the high frequency wave transfer part is disposed on the tip end portion 220 and may face the skin during skin treatment using the handpiece 10.

Meanwhile, as an embodiment, with reference to FIG. 3, the high frequency wave transfer part 320 may include a cover layer 250. The cover layer 250 may be a dielectric substance. When the dielectric substance is applied to an entire surface of the high frequency wave transfer part 320, during skin treatment, the high frequency wave transfer part 320 may transfer the high frequency wave energy by capacitive coupling with the skin. At this time, when the dielectric substance includes, for example, a thermally conductive material such as polyimide, polyurethane, polyethylene, and the like, the high frequency wave transfer part 320 may increase the heat efficiency transferred to the skin in a process in which the high frequency wave energy is transferred to the skin. Accordingly, the cover layer 250 may prevent skin damage caused by a spark caused by direct contact of the high frequency wave transfer part 320 with the skin or a rise in temperature due to an increase in resistance components.

At this time, the cover layer 250 may be applied on an outer surface of the high frequency wave transfer part 320. In this case, the high frequency wave transfer part 320 may transfer the high frequency wave energy to the skin through the cover layer 250 without directly contacting the skin.

At least one high frequency wave transfer part 320 may be provided. As one embodiment, a plurality of high frequency wave transfer parts 320 may be provided. In this case, the plurality of high frequency wave transfer parts 320 may be symmetrically arranged on opposite sides with the ultrasonic wave irradiation surface 230 as a center.

Specifically, the plurality of high frequency wave transfer parts 320 may be arranged in a pair of rows, and the high frequency wave transfer parts 320 of the pair of rows have the ultrasonic wave irradiation surface 230 therebetween and may be arranged side by side in the longitudinal direction (Y axis direction).

As exemplarily shown in the drawing, each row may include eight high frequency wave transfer parts 320, but the present disclosure is not limited thereto. However, for convenience of description, the following description will be made focusing on an embodiment in which eight high frequency wave transfer parts 320 are included in each row.

In such a case, the eight high frequency wave transfer parts 320 included in any one of the pair of rows may be arranged symmetrically one to one with the eight high frequency wave transfer parts 320 included in another one of the pair of rows. In addition, the high frequency wave transfer parts 320 included in each row may be spaced apart from each other by a predetermined distance.

The ultrasonic wave module 400 may generate and transfer ultrasonic wave energy to the skin. The ultrasonic wave module 400 may include an ultrasonic wave generator 410 and an ultrasonic wave transfer part 420.

The ultrasonic wave generator 410 may receive a control signal from the controller 600 to be described later and transfer a received control signal to the ultrasonic wave transfer part 420. An ultrasonic wave may be, for example, high intensity focused ultrasound (HIFU).

As the one embodiment, the ultrasonic wave generator 410 may be disposed inside the main body 20. In such a case, the ultrasonic wave generator 410 may transfer control signals such as frequency, intensity, and the like input by the user to the ultrasonic wave transfer part 420 inside the tip 200. On the other hand, as another embodiment, the ultrasonic wave generator 410 is disposed inside the housing 100, or as yet another embodiment, provided with the ultrasonic wave transfer part 420 and placed inside the housing 100.

The ultrasonic wave transfer part 420 may receive a control signal from the ultrasonic wave generator 410 and generate ultrasonic wave energy to transfer to the skin. The ultrasonic wave transfer part 420 may provide ultrasonic wave energy to the skin through at least a portion of the ultrasonic wave irradiation surface 230. The ultrasonic wave transfer part 420 may be disposed inside the tip body 210. At this time, the ultrasonic wave transfer part 420 is disposed at a position facing the ultrasonic wave irradiation surface 230 inside the tip body 210, whereby the ultrasonic wave energy emitted from the ultrasonic wave transfer part 420 penetrates the ultrasonic wave irradiation surface 230 and may be transferred to the skin being brought into contact with the ultrasonic wave irradiation surface 230.

The ultrasonic wave transfer part 420 may be disposed to be linearly movable along the ultrasonic wave irradiation surface 230. At this time, the ultrasonic wave transfer part 420 may reciprocate and linearly move along the longitudinal direction (Y axis direction) of the ultrasonic wave irradiation surface 230 by the movement part 500 and change a position where the ultrasonic wave energy is emitted.

The movement part 500 may be disposed inside the handpiece 10 to move the ultrasonic wave transfer part 420.

The movement part 500 may include a motor 510, the guide shaft 520, and a connection member 530.

The motor 510 may provide a driving force for moving the ultrasonic wave transfer part 420 and the connection member 530. The motor 510 may be, for example, a linear motor. The ultrasonic wave transfer part 420 and the connection member 530 may be linearly moved by the motor.

The motor 510 may be located inside the housing 100. The motor 510 is disposed above the guide shaft 520 and the connection member 530 but may be connected to the connection member 530, thereby moving the connection member 530.

The guide shaft 520 may guide the movement paths of the ultrasonic wave transfer part 420 and the connection member 530. By the guide shaft 520, the ultrasonic wave transfer part 420 and the connection member 530 may be linearly moved one way or reciprocally along the longitudinal direction (Y axis direction or −Y axis direction) of the ultrasonic wave irradiation surface 230. In addition, the guide shaft 520 is coupled to the connection member 530 and, when the connection member 530 moves linearly by the motor 510, may provide stability so that the connection member 530 may move without being shaken.

The guide shaft 520 may be located inside the tip 200. The guide shaft 520 is disposed between the motor 510 and the connection member 530 so that the ultrasonic wave transfer part 420 and the connection member 530 may linearly move along the ultrasonic wave irradiation surface 230. The guide shaft 520 may have a length the same as the ultrasonic wave irradiation surface 230.

The connection member 530 may be connected to the ultrasonic wave transfer part 420 and the guide shaft 520, thereby linearly moving the ultrasonic wave transfer part 420. In addition, the connection member 530 may be coupled in a shape surrounding an outer surface of the ultrasonic wave transfer part 420, thereby protecting the ultrasonic wave transfer part 420.

The connection member 530 may be disposed between the ultrasonic wave transfer part 420 and the guide shaft 520, at the inside of the tip 200. As the motor 510 operates, the connection member 530 linearly moves along the guide shaft 520, and the ultrasonic wave transfer part 420 connected to the connection member 530 may also linearly move and emit ultrasonic wave energy.

Whether to move/stop, a moving direction, and a moving time for the movement part 500 may be controlled on the basis of a control signal transferred from the controller 600, which will be described in detail later.

The controller 600 may control the high frequency wave module 300, the ultrasonic wave module 400, and the movement part 500. At this time, the controller 600 may be implemented in a form of, for example, a circuit board mounted on a computer for controlling the handpiece 10, a computer chip mounted on a circuit board, software embedded in a computer chip or embedded in a control computer, or the like.

The controller 600 may include a user interface. The controller 600 may receive input information such as whether to generate high frequency wave energy and ultrasonic wave energy, emission time point, frequency and intensity, a pulse interval, and the like from the user. The controller 600 may control the high frequency wave module 300 and the ultrasonic wave module 400 according to input information provided by the user and control generation and emission of the high frequency wave energy and ultrasonic wave energy.

The controller 600 may control a transfer method of the high frequency wave energy emitted from the high frequency wave transfer part 320 with one of bipolar and monopolar. The present disclosure is not limited thereto, and as another embodiment, a high frequency wave energy transfer method may be unipolar or multipolar.

The bipolar method may be a method in which high frequency wave energy emitted from one high frequency wave transfer part 320 enters another high frequency wave transfer part 320. The high frequency wave transfer parts 320 are at least two, and therethrough, the controller 600 may allow transfer and recovery of the high frequency wave energy to be performed.

The monopolar method may be a method in which high frequency wave energy from the high frequency wave transfer part 320 passes through the patient's body and enters a ground patch. In this case, the handpiece 10 may include one ground patch. At this time, the ground patch is attached to a portion of a patient's skin surface, and the controller 600 may transfer high frequency wave energy through the high frequency wave transfer part 320.

The controller 600 may control an emission sequence of the high frequency wave energy from a plurality of high frequency wave transfer parts 320.

For example, as described above, eight high frequency wave transfer parts 320 may be provided, and for convenience of explanation, the eight high frequency wave transfer parts 320 will be referred to as a first high frequency wave transfer part 320a, a second high frequency wave transmission part 320b, a third high frequency wave transfer part 320c, a fourth high frequency wave transfer part 320d, a fifth high frequency wave transfer part 320e, a sixth high frequency wave transfer part 320f, a seventh high frequency wave transfer part 320g, and an eighth high frequency wave transfer part 320h. At this time, the first to eighth high frequency wave transfer parts 320a, 320b, 320c, 320d, 320e, 320f, 320g, and 320h may be sequentially disposed on the tip end portion 220 along the longitudinal direction (Y axis direction) of the ultrasonic wave irradiation surface 230.

As one embodiment, the controller 600 may control the high frequency wave energy to be emitted according to an arrangement order of the high frequency wave transfer parts 320. Specifically, the controller 600 may control the high frequency wave energy to be sequentially emitted at the second to eighth high frequency wave transfer parts 320b, 320c, 320d, 320e, 320f, 320g, and 320h after the first high frequency wave transfer part 320a emits the high frequency wave energy for the first time.

At this time, the controller 600 may control the emission time point of the high frequency wave energy of each high frequency wave transfer part 320. For example, with reference to a part (a) of FIG. 7, the controller 600 may control the high frequency wave energy to be continuously emitted without a delay time Dt in between pulses of each high frequency wave transfer part 320. More specifically, the controller 600 may control the pulse of the second high frequency wave transfer part 320b to start at a time point when the pulse of the first high frequency wave transfer part 320a ends. The pulses of the third to eighth high frequency wave transfer parts 320c, 320d, 320e, 320f, 320g, and 320h may operate the same as the pulse of the first high frequency wave transfer part 320a and the pulse of the second high frequency wave transfer part 320b.

As another example, with reference to a part (b) of FIG. 7, the controller 600 may control a delay time to occur in between pulses of each high frequency wave transfer part 320. More specifically, the controller 600 may control such that pulse generation is delayed for a specific time from a time point when the pulse of the first high frequency wave transfer part 320b ends to a time point when the pulse of the second high frequency wave transfer part 320b starts. The pulses of the third to eighth high frequency wave transfer parts 320c, 320d, 320e, 320f, 320g, and 320h may operate the same as the pulse of the first high frequency wave transfer part 320a and the pulse of the second high frequency wave transfer part 320b.

As still another example, with reference to a part (c) of FIG. 7, the controller 600 may control the pulses of the high frequency wave transfer parts 320 not to have a delay time in between but to overlap each other. More specifically, the controller 600 may control the pulse of the second high frequency wave transfer part 320b to start before the pulse of the first high frequency wave transfer part 320a ends so that the pulses partially overlap each other. The pulses of the third to eighth high frequency wave transfer parts 320c, 320d, 320e, 320f, 320g, and 320h may operate the same as the pulse of the first high frequency wave transfer part 320*a* and the pulse of the second high frequency wave transfer part 320*b*.

As shown in FIG. 7, while each high frequency wave transfer part 320 emits high frequency wave energy, the ultrasonic wave transfer part 420 may also linearly move and allow the ultrasonic wave energy to be sequentially irradiated. At this time, the skin may be simultaneously irradiated with high frequency wave energy and ultrasonic wave energy.

As another embodiment, with reference to FIG. 8, when the same high frequency wave transfer parts 320 are disposed on opposite sides with the horizontal center line 221 as a reference, respectively, the controller 600 may control the same high frequency wave transfer parts 320 to emit high frequency wave energy at the same time.

At this time, when the controller 600 controls the high frequency wave energy transfer method of the high frequency wave transfer part 320 in a bipolar manner, high frequency wave energy may be emitted and recovered by the same high frequency wave transfer parts 320 themselves. For example, the high frequency wave energy emitted from the first high frequency wave transfer part 320*a* may be recovered by the symmetrical first high frequency wave transfer part 320*a*.

The controller 600 may control the skin to be irradiated with high frequency wave energy and ultrasonic wave energy at the same time or at different times, respectively. In this case, for example, while the ultrasonic wave transfer part 420 emits ultrasonic wave energy during moving in the direction from left to right (Y axis direction) on the drawing as shown in a part (b) of FIG. 8, the controller 600 may control such that one high frequency wave transfer part emits high frequency wave energy and another high frequency wave transfer part 320 neighboring the one high frequency wave transfer part recovers the high frequency wave energy. At this time, when the high frequency wave transfer part 320 is present at an irradiation point of the ultrasonic wave energy, the high frequency wave energy and ultrasonic wave energy may be transferred to the skin at the same time, or only one of the high frequency wave energy and ultrasonic wave energy may be transferred to the skin. As another example, while the ultrasonic wave transfer part 420 emits ultrasonic wave energy during moving in the direction from left to right (Y axis direction) on the drawing as shown in a part (b) of FIG. 8, the controller 600 controls such that high frequency wave energy is emitted in the order from the eighth high frequency wave transfer part 320*h* to the first high frequency wave transfer part 320*a*, but the high frequency wave energy of each of the high frequency wave transfer parts is recovered by another high frequency wave transfer part 320 neighboring the one high frequency wave transfer part. Accordingly, emission orders of the ultrasonic wave energy and high frequency wave energy are opposite, so the skin may be irradiated with the high frequency wave energy and the ultrasonic wave energy at different times. At this time, when the high frequency wave transfer part 320 is present at an irradiation point of the ultrasonic wave energy, the high frequency wave energy and ultrasonic wave energy may be transferred to the skin at the same time, or only one of the high frequency wave energy and ultrasonic wave energy may be transferred to the skin.

Through this, it is possible to prevent burns from occurring due to an increase in temperature of the skin irradiated with ultrasonic wave energy and high frequency wave energy, maximize the effect of treatment, and shorten the treatment time.

The controller 600 may control the emission and recovery of high frequency wave energy between the same high frequency wave transfer parts 320. For example, the high frequency wave energy emitted from the first high frequency wave transfer part 320*a* is recovered with another first high frequency wave transfer part 320*a*, and the high frequency wave energy emitted from the second high frequency wave transfer part 320*b* may be recovered with another second high frequency wave transfer part 320*b*. The third to eighth high frequency wave transfer parts 320*c*, 320*d*, 320*e*, 320*f*, 320*g*, and 320*h* may operate in the same way as the first high frequency wave transfer part 320*a* and the second high frequency wave transfer part 320*b*.

As still another embodiment, the high frequency wave transfer parts 320 may disposed to be the same on left and right sides, respectively, with a vertical center line 222 as a reference. For example, with reference to FIG. 9, the first to fourth high frequency wave transfer parts 320*a*, 320*b*, 320*c*, and 320*d*, each of which consists in a pair, may be disposed to be equal on the left and right sides with the vertical center line 222 as the reference. In this case, the controller 600 may control such that the same high frequency wave transfer parts 320 emit high frequency wave energy having the same frequency and energy.

In addition, when the ultrasonic wave energy is emitted while the ultrasonic wave transfer part 420 moves in the direction from left to right in FIG. 9 (Y axis direction), the same high frequency wave transfer parts 320 each emit high frequency wave energy. At this time, the controller 600 may control such that the high frequency wave transfer parts 320 located on a rear side row output high frequency wave energy prior to ultrasonic wave energy. On the other hand, when the ultrasonic wave transfer part 420 is individually located in each high frequency wave transfer part 320, the controller 600 may control high frequency wave energy and ultrasonic wave energy to be irradiated at the same time.

The controller 600 may group and control a plurality of high frequency wave transfer parts 320. The controller 600 may control an operation of each group and may also individually control the operation of each of the high frequency wave transfer parts 320 in each group. For example, with reference to FIG. 10, it may be divided such that the first to fourth high frequency wave transfer parts 320*a*, 320*b*, 320*c*, and 320*d* are a first group G1, and the fifth to eighth high frequency wave transfer parts 320*e*, 320*f*, 320*g*, and 320*h* are a second group G2. In this case, with a direction, which faces the right from the left, as a reference, the high frequency wave transfer parts 320 may be arranged and grouped to be the same each other on opposite sides. The controller 600 may allow the first group to emit high frequency wave energy or only the first high frequency wave transfer parts 320*a* of the first group to emit high frequency wave energy.

Although the controller 600 controls the plurality of high frequency wave transfer parts 320 by dividing the same into two groups, this is only one embodiment of the present disclosure, and the controller 600 may allow the groups of the high frequency wave transfer parts 320 to be configured in various ways to be controlled.

As described above, the handpiece 10 according to the embodiments of the present disclosure includes: a housing 100; a tip 200 disposed at one end of the housing 100; a plurality of high frequency wave transfer parts 320 disposed on the tip 200 and configured to transfer high frequency wave energy to skin in a pulsed manner; an ultrasonic wave transfer part 420 disposed on the tip 200, but spaced apart from the high frequency wave transfer parts 320, and configured to transfer generated ultrasonic wave energy through an ultrasonic wave irradiation surface 230 provided on the tip 200 to the skin; and a movement part 500 disposed inside the housing 100 or the tip 200 and configured to move the ultrasonic wave transfer part 420 along the ultrasonic wave irradiation surface 230. Accordingly, the handpiece 10 may allow the high frequency wave energy and ultrasonic wave energy to be transferred to the skin with one handpiece 10 without continuous movement of the handpiece 10.

Through this, the skin is treated and improved by maximizing the thermal effect of the high frequency wave energy and ultrasonic wave energy transferred to the skin, and damage to the skin may not be applied even when the skin is irradiated with the high frequency energy and the ultrasonic energy at the same time.

The above description of the present disclosure is for illustrative purposes, and those skilled in the art will be able to understand that it may be easily modified into other specific forms without changing the technical spirit or essential features of the present disclosure. Therefore, the embodiments described above should be understood as illustrative in all respects and not limiting. For example, each component described as a single type may be implemented as being distributed, and similarly, components described as having been distributed may be implemented in a combined form.

The scope of the present disclosure is indicated by the following claims, and all changes or modifications derived from the meaning and scope of the claims and equivalent concepts should be interpreted as being included in the scope of the present disclosure.

What is claimed is:

1. A high frequency wave and ultrasonic wave fusion treatment device, the device comprising:
    a housing;
    a tip disposed at one end of the housing;
    a plurality of high frequency wave transfer parts disposed on the tip and configured to transfer high frequency wave energy to skin in a pulsed manner;
    an ultrasonic wave transfer part disposed on the tip, but spaced apart from the high frequency wave transfer parts, and configured to transfer generated ultrasonic wave energy through an ultrasonic wave irradiation surface provided on the tip to the skin, the ultrasonic wave irradiation surface having an elongated shape elongated in an extension direction; and
    a movement part disposed inside the housing or the tip and configured to move the ultrasonic wave transfer part along the extension direction of the ultrasonic wave irradiation surface; and
    a controller configured to control at least one of the high frequency wave transfer parts, the ultrasonic wave transfer part, and the movement part,
    wherein the controller is configured to control an emission sequence of the high frequency wave energy of each of the high frequency wave transfer parts based on a movement direction of the ultrasonic wave transfer part in the extension direction.

2. The device of claim 1, wherein the plurality of high frequency wave transfer parts is arranged symmetrically on opposite sides with the ultrasonic wave irradiation surface as a center.

3. The device of claim 1, wherein the high frequency wave transfer parts are provided with one cover layer disposed on a surface of one side thereof facing the skin,
    wherein the one cover layer includes a thermally conductive material selected from a group consisting of polyimide, polyurethane, and polyethylene.

4. The device of claim 1, wherein the controller is configured to control the high frequency wave transfer parts and the ultrasonic wave transfer part so that the high frequency wave energy and the ultrasonic wave energy are emitted at the same time or at different times, respectively.

5. The device of claim 1, wherein the controller is configured to control the emission sequence and an emission time point of the high frequency wave energy of each of the high frequency wave transfer parts on the basis of an arrangement order of the plurality of high frequency wave transfer parts.

6. The device of claim 5, wherein the controller is configured to control at least one pair of the high frequency wave transfer parts disposed symmetrically with each other with respect to the ultrasonic wave irradiation surface among the plurality of high frequency wave transfer parts to simultaneously emit high frequency wave energy.

7. The device of claim 5, wherein the controller is configured to control a movement distance and a movement time of the movement part such that the emission sequence and emission time point of the high frequency wave energy correspond to the movement distance and the movement time of the movement part according to a predetermined correspondence relationship.

8. The device of claim 7, wherein the controller is configured to control movement of the movement part so that the ultrasonic wave transfer part emits ultrasonic wave energy at a position staggered with the high frequency wave transfer part emitting high frequency wave energy among the plurality of high frequency wave transfer parts.

9. The device of claim 1, wherein the controller is configured to group the plurality of high frequency wave transfer parts into a plurality of groups and control emission of the high frequency wave energy for each group.

10. The device of claim 9, wherein the controller is configured to control an emission sequence and an emission time point of the high frequency wave energy on the basis of an arrangement order of the plurality of groups.

11. The device of claim 1,
    wherein the high frequency wave transfer parts are arranged at both sides of the elongated shape and include a first pair of high frequency wave transfer parts from among the plurality of the high frequency wave transfer parts located adjacent to one end of the elongated shape and a second pair of high frequency wave transfer parts from among the plurality of the high frequency wave transfer parts located adjacent to an opposite end of the elongated shape,
    wherein the controller is configured to control such that the high frequency wave energy is emitted in an order of a direction either from the first pair of high frequency wave transfer parts toward the second pair of high frequency wave transfer parts or from the second pair of high frequency wave transfer parts toward the first pair of high frequency wave transfer parts, based on the movement direction of the ultrasonic wave transfer part in the extension direction of the elongated shape.

\* \* \* \* \*